United States Patent [19]

Hosaka et al.

[11] 4,308,110

[45] Dec. 29, 1981

[54] PROCESS FOR SEPARATION AND PURIFICATION OF DIHYDRIC PHENOLS

[75] Inventors: Hirokazu Hosaka, Ibaraki; Kunihiko Tanaka, Toyonaka; Toshiharu Morita, Yao; Katsuyuki Shiota, Toyonaka; Yuji Ueda, Izumi, all of Japan

[73] Assignee: Sumitomo Chemical Company Limited, Osaka, Japan

[21] Appl. No.: 193,588

[22] Filed: Oct. 3, 1980

[30] Foreign Application Priority Data

Oct. 9, 1979 [JP] Japan ............................. 54/130364
Oct. 9, 1979 [JP] Japan ............................. 54/130365

[51] Int. Cl.$^3$ ..................... B01D 3/38; C07C 39/08
[52] U.S. Cl. .................................. 203/48; 203/73; 203/92; 568/753
[58] Field of Search ..................... 203/48, 92–96, 203/97, 71, 73; 568/753, 750, 751; 260/707

[56] References Cited

U.S. PATENT DOCUMENTS

| | | | |
|---|---|---|---|
| 1,912,628 | 6/1933 | Elliott | 203/48 |
| 3,900,523 | 8/1975 | Tada et al. | 568/753 |
| 3,929,910 | 12/1975 | Suda et al. | 568/751 |
| 3,968,171 | 7/1976 | Burkholder et al. | 568/753 |
| 4,049,723 | 9/1977 | Tanaka et al. | 568/753 |
| 4,119,791 | 10/1978 | Hollingshead et al. | 568/753 |

*Primary Examiner*—Wilbur L. Bascomb, Jr.
*Attorney, Agent, or Firm*—Stevens, Davis, Miller & Mosher

[57] ABSTRACT

Highly decolorized, purified hydroquinone and resorcinol can be separated from each other from a mixture containing hydroquinone and resorcinol and recovered by continuously rectifying the mixture, thereby obtaining rectification bottoms containing resorcinol and hydroquinone in a ratio by weight of resorcinol to hydroquinone of 0.1–1:1 while obtaining resorcinol as a distillate, redistilling the rectification bottoms, contacting hydroquinone vapor with water vapor, condensing the hydroquinone vapor in the presence of the water vapor, thereby recovering hydroquinone as an aqueous hydroquinone solution, and then recrystallizing the aqueous hydroquinone solution, if necessary, in the presence of an organic solvent, thereby separating hydroquinone from the aqueous solution.

5 Claims, No Drawings

PROCESS FOR SEPARATION AND PURIFICATION OF DIHYDRIC PHENOLS

The present invention relates to a process for separation and purification of dihydric phenols, and more particularly to a process for efficiently separating resorcinol and hydroquinone from a mixture containing resorcinol and hydroquinone, and a process for separating and purifying hydroquinone from crude hydroquinone containing impurities by distillation.

In the past resorcinol and hydroquinone were produced independently, and thus it was commercially less necessary to separate resorcinol and hydroquinone from their mixture. However, processes for producing resorcinol and hydroquinone simultaneously have been recently developed, and consequently it has been necessary to separate resorcinol and hydroquinone from each other from a mixture containing resorcinol and hydroquinone.

As a process for separating resorcinol and hydroquinone from each other, a recrystallization process using a specific solvent such as methanol, etc. has been known (Japanese published examined patent application No. 12500/1978), where resorcinol must be separated from hydroquinone by utilizing transfer by a solvent having a pseudo-eutectic point for resorcinol and hydroquinone, and thus the process is not always satisfactory as regards the recovery of high purity product and purification efficiency.

On the other hand, separation of resorcinol and hydroquinone from each other has been regarded as difficult owing to their very close boiling points, high melting points and sublimation tendencies. When a mixture containing resorcinol and hydroquinone is actually fractionated, resorcinol can be separated as a distillate with high purity, whereas hydroquinone with high purity cannot be separated.

Hydroquinone has been so far produced according to various processes and has been widely used as raw materials for photographic reagent, antioxidant for polymers, etc., but is readily susceptible to discoloration, and thus the process for decolorization and purification of hydroquinone has been an important problem. Particularly, a process for producing hydroquinone alone or together with resorcinol simultaneously through hydroperoxide has been recently developed, and the crude hydroquinone obtained according to the process contains a large amount of high boiling impurities and also contains resorcinol in some cases. Thus, decolorization and purification of the crude hydroquinone have been a very important problem that determines the production of hydroquinone itself.

So far well known processes for purifying the crude hydroquinone include recrystallization process, extraction process, etc., but these processes are not always satisfactory. Thus, other processes utilizing pretreatment by a reducing agent, or contact with hydrogen in the presence of a catalyst have been investigated, but all of these processes are complicated in treating operations and are not always satisfactory as regards purification effect.

Under these circumstances, the present inventors have made extensive studies of a process for efficiently separating resorcinol and hydroquinone from each other from a mixture containing resorcinol and hydroquinone and a process for separating and purifying hydroquinone with distinguished decoloration and purification effects, and have established the present invention.

The present invention provides a process for separating resorcinol and hydroquinone from each other from a mixture containing resorcinol and hydroquinone, which comprises continuously rectifying a mixture containing resorcinol and hydroquinone, thereby obtaining rectification bottoms containing resorcinol and hydroquinone in a ratio by weight of resorcinol to hydroquinone of 0.1–1:1, while obtaining resorcinol as a distillate, and recrystallizing the rectification bottoms from at least one of water and an organic solvent, thereby separating hydroquinone from the rectification bottoms, or redistilling the rectification bottoms and recrystallizing a redistillate in at least one of water and an organic solvent, thereby separating hydroquinone from the redistillate, and a process for separating and purifying hydroquinone from crude hydroquinone containing impurities by distillation, which comprises contacting generated hydroquinone vapor with water vapor, and condensing the hydroquinone vapor in the presence of the water vapor, thereby recovering the hydroquinone as an aqueous solution.

The present invention will be described in detail below.

A mixture containing resorcinol and hydroquinone (which will be hereinafter referred to as "RH mixture") to be supplied to a rectification system in the process for separating resorcinol and hydroquinone from each other is a mixture containing resorcinol and hydroquinone as the main components, and can contain a small amount of impurities.

Lower boiling impurities than resorcinol distill off together with resorcinol when rectified in the rectification system, and resorcinol cannot be separated and recovered with high purity. Thus, it is preferable to remove the lower boiling impurities from the mixture in advance.

In the present process it is important to continuously rectify the mixture so that the rectification bottoms may have a ratio by weight of resorcinol to hydroquinone, which will be hereinafter referred to as "R/H", of 0.1–1:1. Rectification of the RH mixture is carried out at a relatively high temperature because both resorcinol and hydroquinone have high boiling points, and consequently thermal deterioration of resorcinol and hydroquinone proceeds. As a result of various studies of conditions for such rectification, the present inventors have found that the thermal deterioration of resorcinol and hydroquinone can be suppressed to a considerably low level by maintaining the R/H ratio of the rectification bottoms at 0.1–1, and the present invention is based on that finding.

Considerable thermal deterioration takes place in an R/H ratio of less than 0.1, and consequently resorcinol and hydroquinone contents are considerably lowered, whereas the content of deterioration products is increased so much in the rectification bottoms that hydroquinone with high purity cannot be easily obtained from such rectification bottoms even if recrystallized, and also the handling of the rectification bottoms becomes difficult owing to the sublimation tendency of the bottoms, etc.

When the R/H ratio of the rectification bottoms exceed 1 on the other hand, the efficiency of recrystallization to separate hydroquinone from the rectification bottoms is considerably decreased, and efficient separation of hydroquinone becomes difficult.

Continuous rectification under the abovementioned conditions permits separation and recovery of resorcinol with high purity as a distillate.

Separation and recovery of hydroquinone from the rectification bottoms are carried out by direct recrystallization of the rectification bottoms, or redistillation of the rectification bottoms, followed by recrystallization of the resulting redistillate. The latter procedure is effective for preventing hydroquinone from discoloration and meets the object of separating and recovering hydroquinone with less discoloration.

The recrystallization is carried out in at least one of water and an organic solvent as a recrystallization solvent. The organic solvent includes alcohols such as methanol, ethanol, propanol, etc.; ketones such as acetone, methylethylketone, methylisopropylketone, methylisobutylketone, etc.; ethers such as isopropylether, tetrahydrofuran, etc.; esters such as ethyl acetate, butyl acetate, etc., and they can be used alone or in mixture of two or more thereof. Water can be used alone or in mixture of the organic solvent. A small amount of salts can be contained. Recrystallization can be carried out in one run or a plurality of runs batchwise or continuously.

Hydroquinone with high purity is separated and recovered as crystals by the recrystallization, and a solution containing resorcinol and hydroquinone is obtained as the filtrate. The filtrate is wholly or partly recycled to the rectification system for the RH mixture, whereby resorcinol and hydroquinone can be efficiently separated from each other, and recovered. In that case, the recycling is carried out by removing the recrystallization solvent and accumulative impurities from the distillate by distillation, extraction or the like, and then supplying the treated filtrate to the rectification system. It is also possible to recycle the filtrate not only directly to the rectification step of the present invention, but also to preceding steps to the rectification step of the present invention, for example, a step of using such recrystallization solvent or a step of removing the recrystallization solvent and impurities, in a process for process for producing resorcinol and hydroquinone.

Crude hydroquinone containing impurities for the process for separating and purifying hydroquinone is the crude hydroquinone produced according to the so far well known various processes, and is not particularly limited, but the present invention is more effectively applied particularly to crude hydroquinone which is produced according to the process through hydroperoxide and usually contains resorcinol in an amount less equal to that of hydroquinone.

In the present invention it is most important to contact hydroquinone vapor generated in a distillation column with water vapor and condense the hydroquinone vapor in the presence of the water vapor. The following procedures can be taken for that purpose.

According to one procedure, the crude hydroquinone is heated to evaporate hydroquinone, and the generated hydroquinone vapor is contacted with water vapor before or at cooling and condensation, and condensed in the presence of the water vapor, thereby obtaining an aqueous hydroquinone solution as a condensate.

According to one mode of the aforementioned procedure, the generated hydroquinone vapor is brought into contact with water or an aqueous hydroquinone solution under such a condition as to generate water vapor by the heat possessed by the hydroquinone vapor, and eventually the hydroquinone vapor can be brought in contact with water vapor and condensed in the presence of water vapor to obtain an aqueous hydroquinone solution.

In generating the hydroquinone vapor according to the foregoing procedure, it is an effective means for decolorization to inject an inert gas such as nitrogen ges, etc. into the distillation system.

According to another procedure, hydroquinone is evaporated by injecting water vapor into the distillation system, preferably, into a distillation bottoms, and the resulting mixture of hydroquinone vapor and water vapor is cooled and condensed, where it is desirable to conduct operation at a bottoms temperature of 200° C. or higher under such a condition that substantially no water remains in the bottoms by superheating water vapor to be injected into the distillation bottoms or by heating the distillation bottoms.

In the foregoing procedure, the injection rate of water vapor depends upon crude hydroquinone composition, heating temperature, degree of pressure reduction, etc., but is usually about 0.1 to about 10 times as large as that of the crude hydroquinone by weight.

When the crude hydroquinone contains lower boiling compounds than hydroquinone as impurities, the lower boiling compounds are removed as initial distillate fraction by distillation in advance, and then, the present process is applied to the resulting crude hydroquinone.

The present process can be carried out under the atmospheric pressure or a subatmospheric pressure, but under a subatmospheric pressure the boiling point of water is lowered, and consequently the temperature of aqueous hydroquinone solution is lowered and hydroquinone is occasionally crystallized out from the aqueous solution. However, this is no trouble at all in the present invention, but is occasionally rather an advantage for a successive operation of separating hydroquinone.

Thus, hydroquinone, which is highly sublimable in the ordinary distillation and difficult to recover, and is susceptible to discloration, can be recovered and obtained in a colorless or less discolored aqueous hydroquinone solution without sublimation according to the present process. The object of the present invention can be attained, irrespectively of continuous and batchwise operation.

The aqueous hydroquinone solution thus obtained according to the present invention can be used as such in other applications, or can be subjected to appropriate well known further treatment, if necessary, to separate hydroquinone with high purity therefrom. For example, substantially colorless hydroquinone with high purity can be obtained by cooling the aqueous solution, crystallizing and recovering hydroquinone.

When the crystallized and recovered hydroquinone has not a satisfactory purity, the hydroquinone is further recrystallized in water or a solvent, whereby colorless hydroquinone with high purity can be obtained.

In the operation of obtaining hydroquinone with high purity from the aqueous hydroquinone solution obtained according to the present invention, it is possible to add a reducing agent, etc. which have been so far regarded as effective for preventing discoloration of hydroquinone, to the aqueous hydroquinone solution. In that case, more decolorized hydroquinone can be expected together with the remarkable effect of the present invention.

Highly decolorized, purified hydroquinone can be separated and recovered by applying the abovementioned process for separating and purifying hydroquinone to the foregoing process for separating resorcinol and hydroquinone from each other, that is, by continuously rectifying a mixture containing resorcinol and hydroquinone, thereby obtaining rectification bottoms containing resorcinol and hydroquinone in a ratio by weight of resorcinol to hydroquinone of 0.1–1:1, while obtaining resorcinol as a distillate, redistilling the rectification bottoms, contacting hydroquinone vapor with water vapor, condensing the hydroquinone vapor in the presence of the water vapor, thereby recovering hydroquinone as an aqueous hydroquinone solution, and then recrystallizing the aqueous hydroquinone solution, if necessary, in the presence of an organic solvent, thereby separating hydroquinone from the aqueous solution.

As described above, resorcinol and hydroquinone can be separated efficiently with high purity from each other by a combination of separative rectification of resorcinol and hydroquinone under the specific condition with recrystallization of the rectification bottoms or redistillate of the rectification bottoms, and furthermore substantially colorless hydroquinone with high purity can be obtained from crude hydroquinone, whose decolorization and purification have been regarded as very difficult according to the conventional process, in a commercially simple operating manner. Thus, the present invention has a very remarkable commercial significance.

The present invention will be described in detail below, referring to Examples, where percentage and parts are by weight.

EXAMPLE 1

A mixture containing resorcinol and hydroquinone in a content ratio of resorcinol to hydroquinone of 7:3 by weight was continuously supplied to a rectification column having a theoretical number of trays of 40 at a rate of 100 parts per hour, and rectified by adjusting a reflux ratio, heating of bottoms, etc. so that a ratio of resorcinol content/hydroquinone content of rectification bottoms (R/H) could be 0.5, and so that the hydroquinone content of the distillate could be less than 0.3%. The distillate vapor was condensed and made into flakes, whereby 55 parts of highly pure resorcinol with a purity of 99.8% (hydroquinone content: 0.2%) was obtained per hour as a flaky solid. On the other hand, 45 parts of rectification bottoms was obtained per hour, and had a resorcinol content of 32.9% and a hydroquinone content of 65.1%. Deterioration products of resorcinol and hydroquinone amounted to 2.0%. Percent retainabilities of resorcinol and hydroquinone at the separative rectification were 99.6% and 98.0%, respectively.

102 parts of water was added to 100 parts of the above-mentioned rectification bottoms, heated and dissolved to obtain an aqueous solution, and then the aqueous solution was gradually cooled down to 30° C. Deposited crystal was filtered in a centrifuge and dried until the crystal thus obtained had a water content of less than 0.1%, whereby 43.8 parts of purified hydroquinone having a hydroquinone purity of 97.5% and a resorcinol content of 2.4% was obtained. Furthermore, the crystal was recrystallized from water as a solvent and dried, whereby highly pure hydroquinone having a hydroquinone purity of more than 99.7% and a resorcinol content of less than 0.2% was obtained.

EXAMPLE 2

100 parts of a resorcinol-hydroquinone mixture containing 75% resorcinol and 23% hydroquinone was continuously supplied per hour to the same rectification column as used in Example 1, and rectified by adjusting a reflux ratio, heating of bottoms, etc. so that the R/H of rectification bottoms could be about 0.25 and the hydroquinone content of distillate could be less than 0.5%.

The distillate vapor was condensed, and made into flakes, whereby 69.2 parts of highly pure resorcinol having a purity of 99.4% (hydroquinone content: 0.4%) was obtained per hour as a flaky solid. On the other hand, 30.8 parts of the rectification bottoms was withdrawn per hour. The rectification bottoms had a resorcinol content of 18.8% and a hydroquinone content of 71.8%, and the content of deterioration products of resorcinol and hydroquinone was 3.2%. Percent retainabilities of resorcinol and hydroquinone at the separative rectification were 99.5% and 97.4%, respectively.

The rectification bottoms was further subjected continuously to simple distillation, and the distillate was recovered by means of water, and gradually cooled down to 30° C. and crystallized. At the simple distillation of the rectification bottoms, 27.9 parts of the distillate was obtained per hour, and 2.9 parts of the bottoms was obtained per hour.

The distillate slurry recovered by means of water and crystallized was filtered in a centrifuge, and dried until the water content reached 0.2%, whereby 15.9 parts of purified hydroquinone having a hydroquinone purity of 98.1% and a resorcinol content of 1.4% was obtained per hour. The resulting crystal was recrystallized from water as a solvent and dried, whereby highly pure hydroquinone having a purity of more than 99.6% and a resorcinol content of less than 0.3% was obtained.

When the rectification bottoms was subjected to the simple distillation by supplying steam at 200° C. to the bottom of the simple distillation system and adjusting heating and the rate of supplying the steam so that the bottom temperature could be kept at 220° C., and when the distillate vapor including water vapor was cooled and condensed, the distillate thus obtained had a composition substantially equal to that of the distillate slurry obtained by recovering the aforementioned simple distilation distillate vapor by means of water. Hydroquinone with a high purity could be obtained through the same treatment as described above.

EXAMPLE 3

A resorcinol-hydroquinone mixture containing 65% of resorcinol and 34% of hydroquinone was continuously supplied to a rectification column having a theoretical number of trays of 40 at a rate of 100 parts per hour, and rectified by adjusting the reflux ratio, heating of bottoms, etc. so that the R/H of the rectification bottoms could be in a range of 0.15 to 0.2, and the hydroquinone content of the distillate could be less than 0.3%.

The distillate vapor was condensed and made into flakes, whereby 58.6 parts of highly pure resorcinol having a resorcinol purity of 99.7% (hydroquinone content: 0.3) was obtained per hour as a flaky solid. On the other hand, 41.4 parts of rectification bottoms was withdrawn per hour, and the rectification bottoms had a resorcinol content of 14.3% and a hydroquinone content of 78.5% and the deterioration products of resorcinol and hydroquinone amounted to 4.8%. Percent retainabilities of resorcinol and hydroquinone at the separative rectification were 99.1% and 95.9%, respectively.

100 parts of the rectification bottoms was dissolved in 113 parts of methylisobutylketone (MIBK) and the resulting solution was gradually cooled down to 30° C. and crystallized. The resulting slurry was filtered in a centrifuge, and the resulting crystal was dried to remove MIBK, whereby 56.7 parts of purified hydroquinone having a hydroquinone purity of 98.3% and a resorcinol content of 1.1% was obtained. The crystal was recrystallized from water as a solvent and dried, whereby more highly pure hydroquinone having a purity of more than 99.7% and a resorcinol content of less than 0.2% was obtained.

When the crystal obtained by the recrystallization from MIBK and the successive filtration in the centrifuge was washed with water in the centrifuge and then dried, highly pure hydroquinone having a purity of 99.3% and a resorcinol content of 0.4% was obtained.

COMPARATIVE EXAMPLE 1

The same resorcinol-hydroquinone mixture as used in Example 1 was continuously supplied to a rectification column having a theoretical number of trays of 40 at a rate of 100 parts per hour, and rectified by adjusting a reflux ratio, heating of bottoms, etc. so that the R/H of rectification bottoms could be in a range of 0.05 to 0.1 and the hydroquinone content of distillate could be less than 0.3%. Distillate vapor was condensed and made into flakes, whereby 66.6 parts of highly pure resorcinol having a purity of 99.8% (hydroquinone content: 0.2%) was obtained per hour as a flaky solid.

On the other hand, 33.4 parts of rectification bottoms was withdrawn per hour, and the rectification bottoms had a resorcinol content of 4.2% and a hydroquinone content of 70.1%, and the deterioration products of resorcinol and hydroquinone amounted to 25.7%. Percent retainabilities of resorcinol and hydroquinone at the separative rectification were 97.0% and 78.3%, respectively.

138 parts of water was added to 100 parts of the rectification bottoms, heated and dissolved to obtain an aqueous solution. Then, the resulting aqueous solution was gradually cooled down to 30° C., and crystallized. The resulting slurry was filtered in a centrifuge, and the resulting crystal was dried until the water content reached 0.1%, whereby hydroquinone having a hydroquinone purity of 92.6% and a resorcinol content of 1.8% and further containing 5.5% of deterioration products of resorcinol and hydroquinone was obtained. Furthermore, the resulting crystal was recrystallized from water as a solvent, and dried, but 0.9% of the deterioration products was still contained, and the hydroquinone purity was 98.8%.

COMPARATIVE EXAMPLE 2

100 parts of a resorcinol-hydroquinone mixture having a ratio of resorcinol to hydroquinone of 7:3 was charged into a glass reactor with a reflux cooler and a stirrer, and a mixed solvent consisting of 33.3 parts of methanol and 3.7 parts of water was added thereto. Temperature was elevated to 75° C. Then, the solution was gradually cooled down to 0° C. with stirring. The resulting slurry was filtered in a centrifuge, whereby 32.3 parts of crystal consisting of 26 parts of hydroquinone, 3 parts of resorcinol, 2.8 parts of methanol, and 0.5 parts of water, and 104.7 parts of a filtrate consisting of 67 parts of resorcinol, 4 parts of hydroquinone, and 30.5 parts of methanol were obtained. The filtrate was distilled at 75° C. to distill off 30.5 parts of methanol, and 12.8 parts of water was added to the liquid residue. The resulting mixture was transferred to a reactor similar to the former, and cooled down to 30° C. with stirring. The resulting slurry was filtered in a centrifuge to separate crystal from filtrate. The resulting crystal was dried to obtain 36 parts of resorcinol. Percent recovery of resorcinol was 51.4%.

32.3 parts of the crystal obtained from the recrystallization at the former first stage was admixed with 48 parts of water, and the resulting mixture was heated at 75° C. to distill off 1.5 parts of methanol together with 3 parts of water. Then, the resulting slurry formed at 30° C. was filtered in a centrifuge. The resulting crystal was dried to obtain 16 parts of hydroquinone crystal.

EXAMPLE 4

100 parts of crude hydroquinone with blackish brown color containing 95% of hydroquinone and 5% of high boiling impurities was charged into a distillation flask with a stirrer and heated. Steam at 120° C. was injected into the distillation flask at the bottom, and hydroquinone was evaporated and distilled off together with steam by adjusting the heating and the rate of steam injection so that the temperature of bottoms coulde be kept at 220° C. Distillate vapor was cooled and condensed, whereby 290 parts of colorless aqueous solution containing 32% of hydroquinone was obtained.

The resulting aqueous solution was cooled, crystallized and filtered, and the resulting crystal was dried, whereby 69 parts of highly pure hydroquinone having a purity of more than 99.5% was obtained.

EXAMPLE 5

100 parts of the same crude hydroquinone as in Example 4 was charged into the same distillation flask as used in Example 4, and heated. Steam at 150° C. was injected into the distillation flask at the bottom, and hydroquinone was evaporated and distilled off together with steam by adjusting the heating and the rate of steam injection so that the temperature of bottoms could be kept at 250° C. Distillate vapor was cooled and condensed, whereby 145 parts of slurry (colorless aqueous phase and white crystal) containing 65% of hydroquinone was obtained.

The resulting slurry was further admixed with water, and recrystallized. The resulting crystal was filtered and dried, whereby 70 parts of colorless, highly pure hydroquinone having a purity of more than 99.5% was obtained.

EXAMPLE 6

100 parts of a crude hydroquinone-resorcinol mixture with blackish brown color containing 80% of hydroquinone, 17% of resorcinol and 3% of high boiling impurities was charged into the same distillation flask as used in Example 4. Steam at 200° C. was injected into the distillation flask at the bottom, and hydroquinone and resorcinol were evaporated and distilled off by adjusting the heating and the rate of steam injection so that the temperature of bottoms could be kept at 230° C. Distillate vapor was cooled and condensed, whereby 229 parts of colorless aqueous solution containing 34% of hydroquinone and 8% of resorcinol was obtained.

The resulting aqueous solution was further admixed with 38 parts of water containing 400 ppm of sodium hydrogen sulfite, and the resulting solution was gradually cooled down to 30° C., and the deposited crystal was filtered and dried, whereby 55.1 part of colorless hydroquinone (purity: 98.7%, resorcinol content: 1.1%) was obtained.

Furthermore, the resulting hydroquinone was recrystallized from water as a solvent under nitrogen atmosphere, filtered and dried, whereby 40 parts of colorless, highly pure hydroquinone having a purity of more than 99.5% was obtained.

EXAMPLE 7

100 parts of the same crude hydroquinone as used in Example 4 was charged into a distillation flask with a stirrer, and heated. Pressure of the distillation system was reduced to 250 mmHg and steam at 150° C. was injected into the distillation flask at the bottom. Hydroquinone was evaporated and distilled off by adjusting the heating and the rate of steam injection so that the temperature of bottoms could be kept at 230° C. Distillate vapor was cooled and condensed, whereby 138 parts of slurry (colorless aqueous phase and white crystal) containing 68% of hydroquinone was obtained.

The resulting slurry was admixed with water containing 100 ppm of oxalic acid, recrystallized, filtered and dried, whereby 70 parts of colorless, highly pure hydroquinone having a purity of more than 99.5% was obtained.

EXAMPLE 8

100 parts of the same crude hydroquinone as used in Example 4 was charged into a distillation flask, and heated. Hydroquinone was evaporated by heating at a temperature of bottoms of 200°14 250° C. under a reduced pressure of 100 mmHg, and steam was added to the hydroquinone vapor steam, and then added to the hydroquinone vapor stream, and then both steam and hydroquinone vapor were cooled and condensed. As a result, 419 parts of colorless aqueous solution containing 22% of hydroquinone was obtained. The resulting aqueous solution was cooled, crystallized, and dried, whereby 68 parts of colorless, highly pure hydroquinone having a purity of more than 99.5% was obtained.

EXAMPLE 9

100 parts of the same crude hydroquinone as used in Example 4 was charged into a distillation flask, and hydroquinone was evaporated by heating at a temperature of bottoms of 200°-250° C. under a reduced pressure of 60 mmHg.

On the other hand, water was charged into a flask (receptacle) with a reflux cooler and a stirrer, and heated to generate water vapor under a reduced pressure of 60 mmHg.

The gas phase part of the distillation flask was communicated with the gas phase part of the receptacle and the hydroquinone vapor was introduced into the gas phase part of the receptacle from the distillation flask to contact the hydroquinone vapor with the water vapor in the receptacle, and condense the hydroquinone vapor at the same time. As a result, 342 parts of slurry containing deposited crystal of hydroquinone was obtained in the receptacle. The resulting slurry was further cooled, filtered and dried, whereby 68 parts of colorless, highly pure hydroquinone having a purity of more than 99.4% was obtained.

EXAMPLE 10

100 parts of the same crude hydroquinone-resorcinol mixture as used in Example 6 was charged into a distillation flask, and nitrogen at 200° C. was injected into the distillation flask at the bottom. Hydroquinone and resorcinol were evaporated and distilled off by adjusting the heating and the rate of nitrogen injection so that the temperature of bottoms could be kept at 230° C.

Mixed hydroquinone and resorcinol vapors were brought into contact with water at a temperature of nearly 100° C., and condensed, and the generated steam was condensed and recovered in an aftercondenser. As a result, substantially same aqueous solution of hydroquinone and resorcinol as in Example 6 was obtained, and treated in the same manner as in Example 3, whereby colorless hydroquinone was obtained.

What is claimed is:

1. A process for separating resorcinol and hydroquinone from each other from a mixture containing resorcinol and hydroquinone, which comprises continuously rectifying a mixture containing resorcinol and hydroquinone, thereby obtaining rectification bottoms containing resorcinol and hydroquinone in a ratio by weight of resorcinol to hydroquinone of 0.1-1:1, while obtaining resorcinol as a distillate, and recrystallizing the rectification bottoms from at least one of water and an organic solvent, thereby separating hydroquinone from the rectification bottoms.

2. A process according to claim 1, wherein the rectification bottoms are first redistilled, and the resulting redistillate is then recrystallized from at least one of water and an organic solvent, thereby separating hydroquinone from the redistillate.

3. A process according to claim 2, wherein the rectification bottoms are redistilled, the resulting hydroquinone vapor is brought into contact with water vapor and condensed in the presence of the water vapor, thereby recovering hydroquinone as an aqueous hydroquinone solution, and then the aqueous solution is recrystallized in the presence or absence of an organic solvent, thereby separating hydroquinone from the aqueous solution.

4. A process for separating and purifying hydroquinone from crude hydroquinone containing impurities by distillation, which comprises contacting generated hydroquinone vapor with water vapor and condensing the hydroquinone vapor in the presence of the water vapor, thereby recovering the hydroquinone as an aqueous solution.

5. A process for separating resorcinol and hydroquinone from each other from a mixture containing resorcinol and hydroquinone, which comprises continusouly rectifying a mixture containing resorcinol and hydroquinone, thereby obtaining rectification bottoms containing resorcinol and hydroquinone in a ratio by weight of resorcinol to hydroquinone of 0.1-1:1, while obtaining resorcinol as a distillate, redistilling the rectification bottoms, contacting hydroquinone vapor with water vapor, condensing the hydroquinone vapor in the presence of the water vapor, thereby recovering hydrqouinone as an aqueous hydroquinone solution, and then recrystallizing the aqueous hydroquinone solution, in the presence or absence of an organic solvent, thereby separating hydroquinone from the aqueous solution.

* * * * *